United States Patent [19]

Meili

[11] Patent Number: 5,130,096
[45] Date of Patent: Jul. 14, 1992

[54] TITRATING SYSTEM INCLUDING PULSE LENGTH MODULATION MEANS

[75] Inventor: Fritz Meili, Madetswil, Switzerland

[73] Assignee: Mettler-Toledo AG, Greifensee, Switzerland

[21] Appl. No.: 500,420

[22] Filed: Mar. 28, 1990

[30] Foreign Application Priority Data

Apr. 4, 1989 [CH] Switzerland .................. 1222/89

[51] Int. Cl.⁵ .................. G01N 31/16; G01N 1/10
[52] U.S. Cl. .................. 422/75; 422/81; 422/100; 436/163; 436/180
[58] Field of Search .................. 422/81, 100, 75; 436/51, 163, 180

[56] References Cited

U.S. PATENT DOCUMENTS

| | | | |
|---|---|---|---|
| 3,319,840 | 5/1967 | Oehme et al. | 422/100 |
| 3,798,431 | 3/1974 | Schulkind et al. | 422/76 |
| 3,909,203 | 9/1975 | Young et al. | 422/67 |
| 3,937,615 | 2/1976 | Clack et al. | 422/62 |
| 4,166,483 | 9/1979 | Nordlund | 422/67 |
| 4,223,558 | 9/1980 | Schmider et al. | 422/100 |
| 4,345,483 | 8/1982 | Paletta et al. | 422/100 |
| 4,710,355 | 12/1987 | Ushikubo | 422/81 |
| 4,873,057 | 10/1989 | Robertson et al. | 422/75 |
| 4,891,185 | 1/1990 | Goldin | 422/101 |
| 4,950,610 | 8/1990 | Tittle | 436/163 |
| 4,952,372 | 8/1990 | Huber | 422/82.09 |

Primary Examiner—Robert J. Warden
Assistant Examiner—T. A. Trembley, II
Attorney, Agent, or Firm—Laubscher & Laubscher

[57] ABSTRACT

A titrating system includes a pulse length modulator for controlling a drive train including a DC drive motor to supply a given dosage of a titrating agent to a specimen. The pulse length modulator is so designed that the drive motor is supplied with DC-current pulses having a constant amplitude, the lengths of the pulses being a function of the start-up characteristic of the drive apparatus. In order to produce the simultaneous dosing of two different titration agents, at least two dosing arrangements and at least two drive trains are provided, thereby affording a joint control-train pair for the alternate selection of the drives. By virtue of the combination of several control-train pairs, a large number of simultaneously selectable pairs of supply devices can be provided. In a preferred embodiment, the pulse length modulator supplies to the electromechanical drive apparatus DC voltage pulses having a generally constant amplitude.

6 Claims, 4 Drawing Sheets

TITRATING SYSTEM INCLUDING PULSE LENGTH MODULATION MEANS

BRIEF DESCRIPTION OF THE PRIOR ART

This invention relates to a titrating system including electrically-operable dosing means for supplying predetermined quantities of a titrating agent to a specimen.

In performing titrations, especially in routine performance, such as it is used in quality controls, for example, in the essential foods industry, in clinical chemistry, or in environmental protection, it is frequently necessary to use different titration agents and/or changing concentrations of titration agents. Here there is an increasing need for titration apparatus that, on the one hand, will permit the simultaneous performance of at least two different titrations, or the sequential performance of a large number of titrations accompanied by extensive automation and, on the other hand, supply results with a high degree of accuracy, that is to say, a dosing of the titration agent down to the very smallest volumes, for example, in the range of 1 $\mu$l.

As a rule, the titration agent is dosed by means of motor-driven piston burets. To prevent inaccuracies, especially in the range of very small volumes, caused by the inertia of the motor, which means that, when very short current surges are supplied, the rotor of the motor does not run through the full rotation angle corresponding to the duration of the current surge, it has been proposed according to Swiss Patent No. 408,468, (which corresponds with the U.S. Pat. to Oehme et al U.S. Pat. No. 3,319,840) to use a stepping motor, supplied by a pulse generator, for the piston drive. In this way, one can achieve exact dosing of very small titration agent volumes. One drawback of this known system is that the buret, described in the above-mentioned Swiss patent, is not suitable for the simultaneous performance of at least two different titrations or the sequential performance of a large number of different titrations in an extremely short time sequence.

The purpose of the present invention is to create a titration apparatus which will permit the simultaneous or at least approximately simultaneous performance of several titrations coupled with extensive automation, which will meet the highest requirements for measurement accuracy, and which can be adapted to the particular requirements by the user without any difficulties.

SUMMARY OF THE INVENTION

Accordingly, a primary object of the present invention is to provide a titrating system including electromechanical dosing means for supplying a titrating agent to a specimen, wherein a direct-current drive motor is supplied by pulse length modulating means with DC pulses (i.e., DC current or voltage pulses) the amplitude of which is constant and the duration of which is a function of the start-up characteristics (i.e., mechanical friction behavior) or inertia of the drive train.

According to a more specific object of the invention, the titrating system includes an electric drive train for operating dosing means for supplying given quantities of the titrating agent to the specimen. An electric motor serves to displace a piston which is contained in the titrating agent supply means and which can be shifted back and forth in a buret cylinder, as shown, for example, in FIG. 3 of the companion Dubs patent application S/N 07,500,410 filed Mar. 28, 1990. As a rule, the drive comprises a DC motor having a threadably connected incremental angular encoder. The motor is connected with the previously mentioned piston via gear and push rod means.

To control the drive, there is provided a pulse length modulation circuit by means of which the direct current motor of the drive means is supplied with DC pulses of constant amplitude, whereby the pulse duration is determined by the start-up characteristic (i.e., mechanical friction behavior) of the drive means, that is to say, the drive train made up of motor, gear, and push rod means. The greater the friction in the elements of the drive train, the greater is the torque requirement of the drive for safe operation.

According to a further object of the invention, the pulse length modulation circuit comprises part of control means which, on the one hand, receives signals supplied, for example, by an incremental angular encoder and, on the other hand, by a detector unit that is integrated into a specimen station, and which converts these signals for the control of the pulse length, that is to say, the turn-on duration of a drive motor, and for the control of the amount of titration agent to be added. In a special case of the pulse length modulation circuit, the input of the circuit is not connected with an incremental angular encoder, but rather a signal is supplied for a constant pulse duration. This simplification is possible if the friction ratios in the drive train are known and if they do not change essentially with the passage of time.

As a consequence of the high regulating accuracy of the drive, this titration system permits the dosing of the very smallest titration agent volumes, something which is expressed also in a measurement accuracy that meets the very highest requirements. This manner of control of the drive means moreover permits extensive automation of the titration process.

According to a more specific object of the invention, the system is operable to control two drive trains from a common pulse length modulation circuit, thereby to afford the simultaneous dosing of two different titration agents because the inertia of the drive trains is so great, or the selection frequency of the pulse length modulation circuit is so high, that both dosing pistons can move simultaneously.

According to still another object, several titrating agent dosing supply means are provided with a corresponding number of drives that are so coupled with a control system that, for the alternating supply of two drives at a time with DC pulses, there is provided one pair of matching control trains and, where the control system is so designed that they can take care of several such pairs of control trains, it is possible sequentially to use a large number of simultaneously selectable pairs of said dosing supply means. In this way, the titration apparatus can be used for the simultaneous performance of several different titration operations.

A further object of the invention is to provide a titration system of the type described above wherein the pulse length modulation means is so designed that the energization duration of each drive means is no greater than 50% of the entire control period. This is particularly advantageous if the mechanical design (gear ratio) of the drive trains is so selected that pulse overlaps can be avoided. For this case, the power supply of the titration system can be designed in an optimum fashion.

According to another object, the pulse length modulation circuit is so designed that the drive can be turned off automatically in case a boundary pulse duration is exceeded, thereby facilitating a trouble-free automatic operation of the titration apparatus because the pulse length modulation circuit is so designed that, in case of the appearance of outside disturbances, such as the blocking of a drive or running against the stop, the drive will automatically be turned off. Here it is particularly advantageous that the apparatus control can be so designed that it can recognize individual disturbances and that it can counter their disturbing effect by turning the particular drive off.

Still another object of the invention is to provide several supply systems having a corresponding number of drives supplied from the pulse length modulator in such a manner that each drive means successively receives DC pulse of constant amplitude and of a length, per operating period T, which corresponds with the quotient of T divided by the number of drive means. This design permits the simultaneous performance of a large number of different titrations because, by means of this design, it is possible to achieve an accurate coordination of the supply of the individual drives with DC pulses. Overlaps or reciprocal impairments of the operating manner of the individual drives and thus of the dosing of the individual titration agents can be excluded from the very beginning by means of this design.

BRIEF DESCRIPTION OF THE DRAWINGS

Other objects and advantages of the present invention will become apparent from a study of the following specification, when viewed in the light of the accompanying drawings, in which.

DETAILED DESCRIPTION

Figure 1:
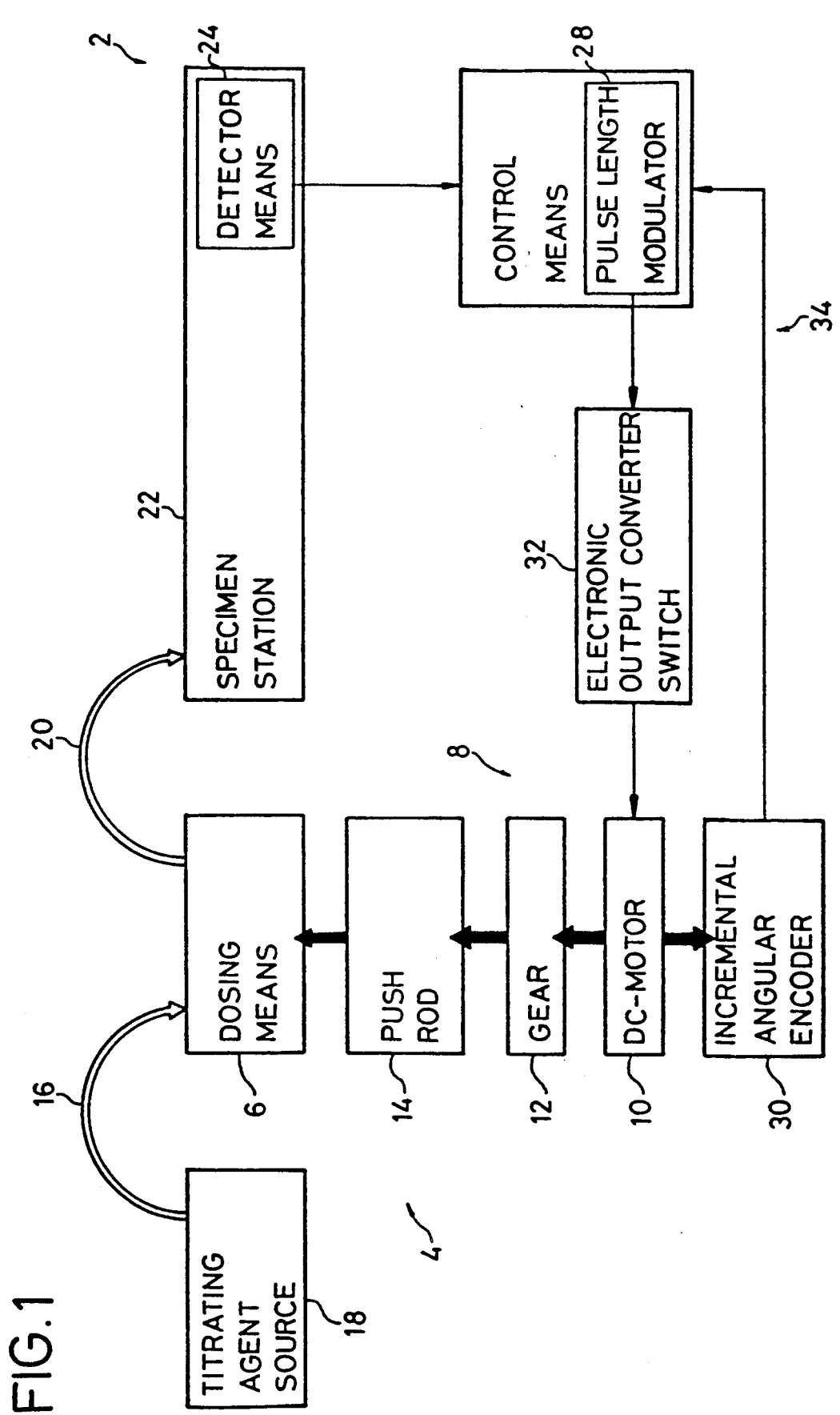
FIG. 1 is a schematic block diagram of a titration system according to the present invention, including a pulse length modulation circuit for controlling the operation of the titrating agent dosage supply means.

Referring first more particularly to FIG. 1, the titration system 2 includes a titrating agent supply means 4 having dosing means 6 for example, including a buret cylinder with a piston that can be shifted in it and a drive train 8 including a drive motor 10, preferably a DC motor, a gear 12, and a push rod 14. Dosing means 6 is connected via a first conduit 16 with a storage vessel 18 containing a titration agent, and via a second hose line 20 with a specimen station 22. Specimen-condition detector means 24 are integrated into the specimen station 22. Signals supplied by detector means 24 are supplied to an apparatus control device 26 into which is integrated a pulse length modulator (PLM) 28. Furthermore, the apparatus control means 26 or the pulse length modulator 28, integrated into it, receives signals from an incremental angular encoder 30 that is coupled with the drive motor 10. Incremental angular encoder 30, which is normally connected with the drive motor 10, as one possible embodiment, includes a circular disc attached to the motor shaft and on the edge of that disc there are uniformly arranged a large number of light-permeable slits, so that, with the help of an optoelectronic scanner, one can generate a corresponding number of electrical pulses per revolution which are sent out as signals and which are fed into the apparatus control means 26.

Figure 3:
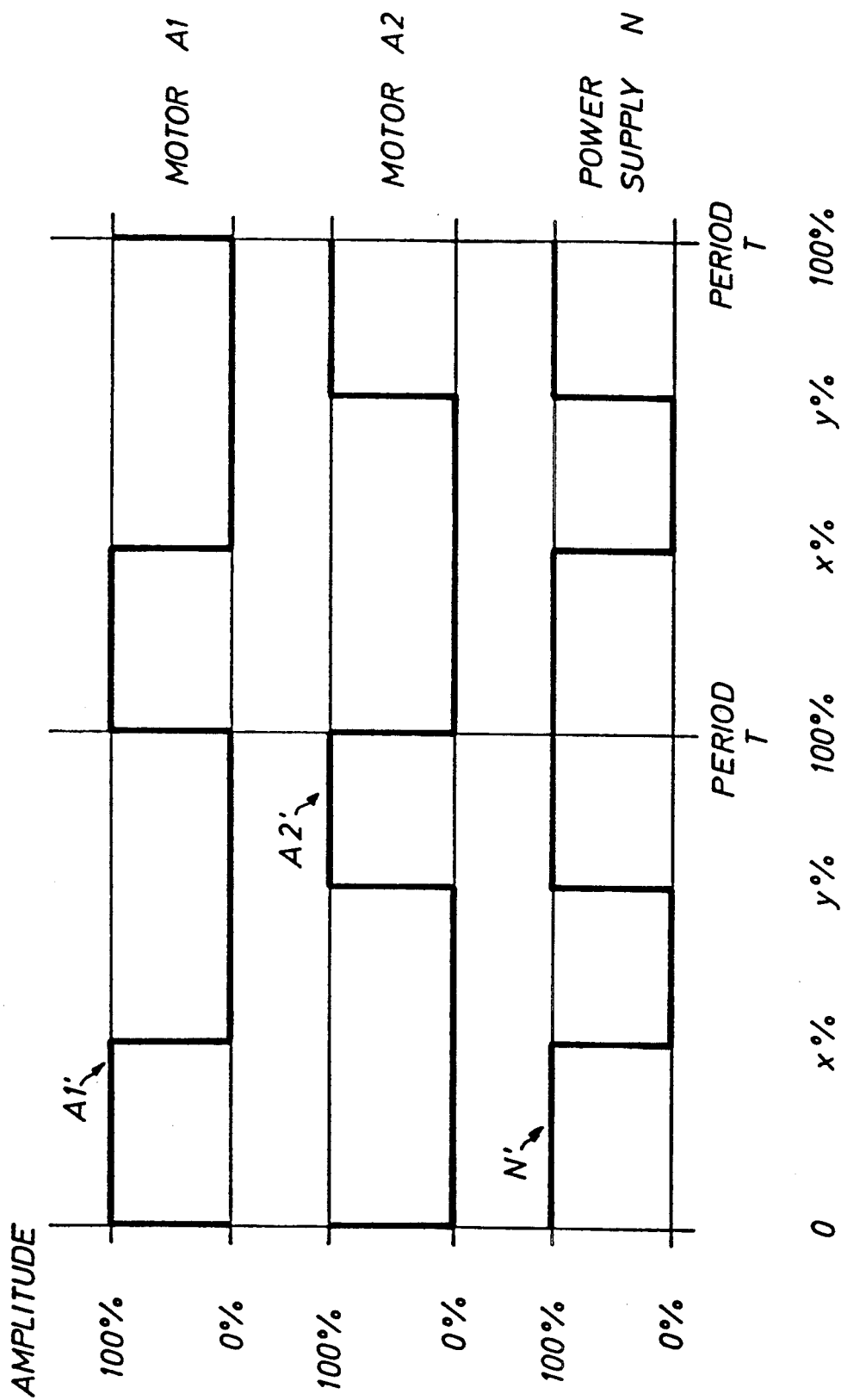
FIG. 3 is a waveform diagram illustrating the operation of the apparatus of FIG. 2.

Pulse length modulator 28 preferably is a regulator which receives, from the incremental angular encoder 30, a signal via the movement of the motor and its rpm and which, from that signal, determines the pulse length, in other words, the turn-on duration per Period T (as illustrated, for example, in the pulse diagram in FIG. 3). The output of this regulator is connected with an electronic output converter switch 32 that again controls the DC motor 10. The dosing quantity is likewise regulated by means of the incremental angular encoder 30. Detector unit 24 sends to the apparatus control means 26 a signal for the quantity of the titration agent to be moved and from that, the apparatus control unit 26 calculates the number of steps by which the drive motor (10) must turn so that the piston, integrated into dosing unit 6, will be shifted by a distance corresponding to the quantity.

After the feedback of the corresponding pulse number from the incremental angular encoder 30 to the apparatus control means 26, drive motor 10 is turned off by the apparatus control means 26 via the electronic output converter switch 32.

The apparatus control unit 26, the pulse length modulator 28, the electronic output converter switch 32, and the angle step transmitter 30 together with the drive motor 10 form a regulating circuit 34. This regulating circuit 34 is connected via drive motor 10 with drive train 8 so that the drive motor 10 can be supplied with DC pulses of constant amplitude by means of pulse length modulator 28, whereby the pulse duration is determined by the start-up characteristic of drive train 8 which comprises drive motor 10, gear 12, push rod 14, and the piston that is integrated into the dosing unit 6.

The pulse length modulator 28 has the following signals available as regulating signals:

(1) the signal of the detector means 24 (after processing in the apparatus control unit 26) for the quantity of the titration agent;

(2) the countable pulses of the incremental angular encoder 30 for the feedback reporting of the end of the dosing operation;

(3) the change of the output level of incremental angular encoder 30 for the detection of motor revolution; and (4) the frequency of incremental angular encoder 30 for the rpm of drive motor 10.

By using all signals, drive motor 10 is so regulated according to a given speed profile that the motor initially will be brought to a predetermined required rpm with constant acceleration, in other words, with a speed rising in a linear fashion. This constant rpm is retained, according to the dosing quantity, until, with constant negative acceleration, one reaches the stopping point which corresponds to the pulse count of incremental angular encoder 30 that belongs to the dosing quantity. The regulating frequency of the motor current is constant, in other words, it is independent of incremental angular encoder 30. In the just described rigid regulation performance with a firmly predetermined speed profile, a firm relationship is also obtained between the dosing quantity and the number of motor current pulses.

If the fluctuations in the frictional behavior of drive train 8 are within a limited, known framework, then one can achieve the same dosing accuracy with a lesser effort on the part of pulse length modulator 28. Drive motor 10 is first of all brought to a predetermined required rpm with the longest permissible current pulses, and is then short-circuited by braking to the desired stopping point. The short-circuit of the drive motor 10 brings about a faster braking than a pure turn-off as a result of the counter-emf generated by the rotation of the rotor in the magnetic field. The required speed must be so selected that step-accurate halting will be possible from all possible operating states of the drive chain 8. In this regulating behavior, the acceleration and braking phase can, depending on the friction, last for different long periods of time at the same dosing quantity. This means that the number of motor current pulses is no longer in a fixed relation to the dosing quantity.

If the friction ratios in the drive train 8 are known and if they do not change essentially with the passage of time, then a further simplification is possible in the sense that the pulse transmitter, which can be programmed as a pulse length modulator 28, is used and it will pass on pulses of constant length—whose length is determined empirically—to the electronic output converter switch 32. In this case, no required rpm in the pulse length modulator 28 is specified in advance; it will develop like the duration of the acceleration and the braking phases, depending on the friction.

The size of the friction of the drive train 8 is in all illustrated cases essential as regards the length of the motor current pulses. To overcome the friction resistances, especially to get from a standstill out of the adhesion friction area into the sliding friction area during movement, the DC motor must produce an adequate output. The mechanical output of the motor upon selection with constant-current pulses arises from the product of the efficiency multiplied by the square of the current and the pulse duration. For output regulation, one can basically use the current and the pulse duration. To keep the switching effort of the pulse length modulator 28 within limits, it is a good idea firmly to adjust the amplitude of the constant current whereby, in the case of several drive trains, which can be selected simultaneously or in sequence, one uses as a foundation the friction of the most sluggish drive trains that are to be operated together. The circuit illustrated schematically in FIG. 2 for the selection for the simultaneous performance of two different titrations includes a central apparatus control unit 36 that is connected with the dispatcher 38. A storage unit 42 is associated with dispatcher 38 which is designed for managing a control-train pair 40. Control-train pair 40 comprises a first control train 44 and a second control train 46. The control trains 44 and 46 comprise pulse length modulators 48 and 48', respectively, and an output transmission stage 50 which, in the case at hand, is made up of drives 52, 54, 56, 58, and 60. Both the central apparatus control means 36 and the dispatchers 38 are microprocessors which contain, in a stored manner, the data required for system control and monitoring, or for the management and monitoring of control-train pair 40, or for retrieving such data from the associated storage unit 42.

Figure 2:
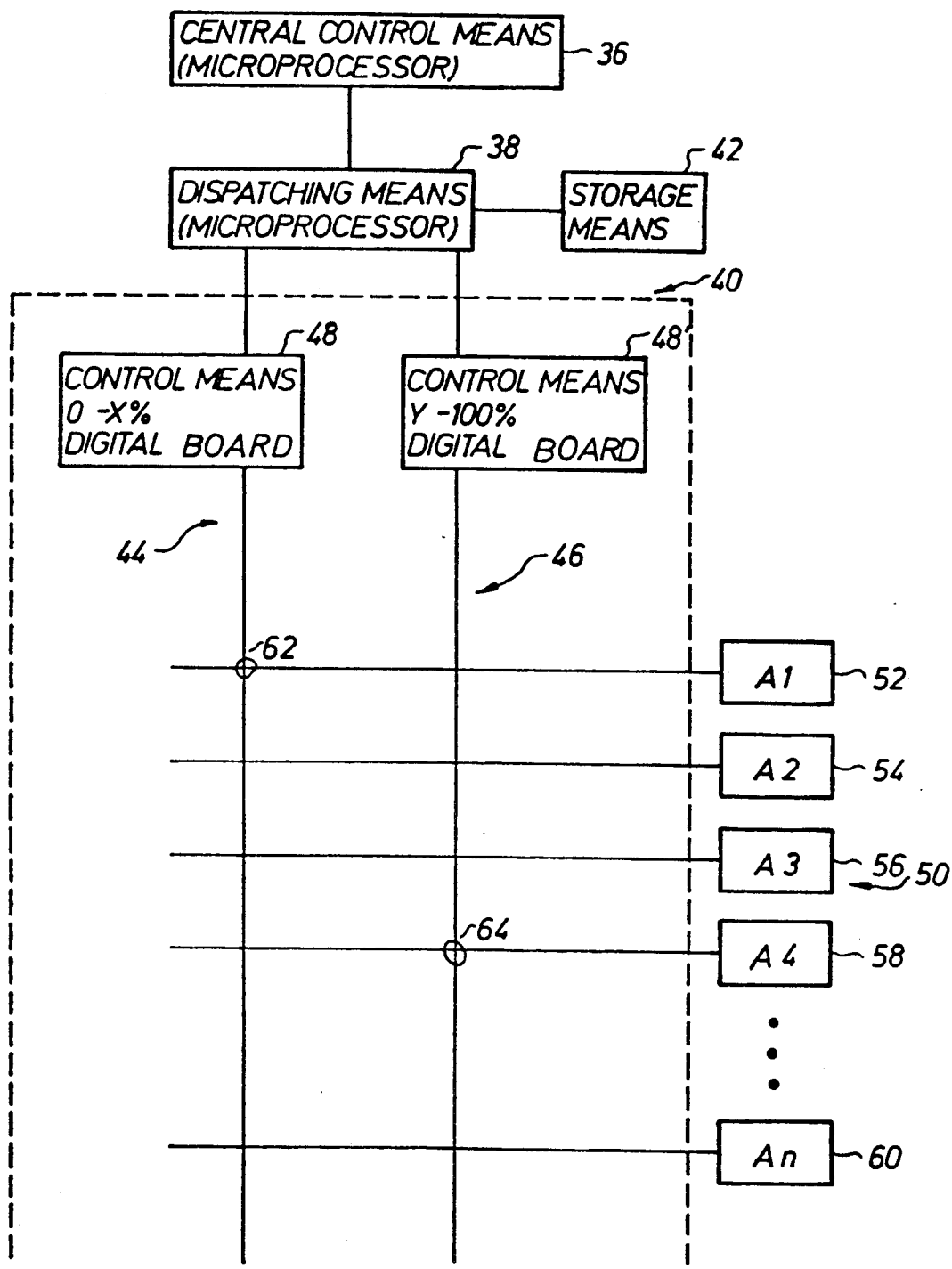
FIG. 2 is a block diagram of a titrating system having a pulse length modulation matrix operable to perform simultaneously two different titrating operations.

FIG. 2 illustrates the possible selection of two drives from a large number n of drives. Here, the first control train 44 is associated with the first drive 52, and the second control train 46 is associated with the fourth drive 58. This matchup can be selected freely, whereby the choice of the drives can be accomplished in a manner similar to the known principle of a cross-bar distributor where the lines from the control train and the lines to the drives are arranged in a rectangular fashion without touching each other. Contacts can then be established at the desired connecting points as indicated by circuit connections 62 and 64.

The pulse diagram according to FIG. 3 illustrates schematically the possible time frame of the alternating power supply N of two drive motors A1 and A2, whereby the real transient buildup oscillation processes are not considered. Plotted on the abscissa is the pulse duration, related to the Period Duration T of the alternating power supply N, and on the ordinate is plotted the amplitude. The curve A1' corresponds with the current/time-curve of the power supply for drive motor A1, while curve A2' corresponds with that part of the current/time-curve of the power supply for drive motor A2. The curve N' shows the sum of both currents vs. time as measurable at the output of the power supply N. From the diagram we can see that the pulse duration in no case is longer than 50% of the period duration, and that the sum of the pulses supplied to drives A1 and A2 is smaller than 100%.

Figure 4:
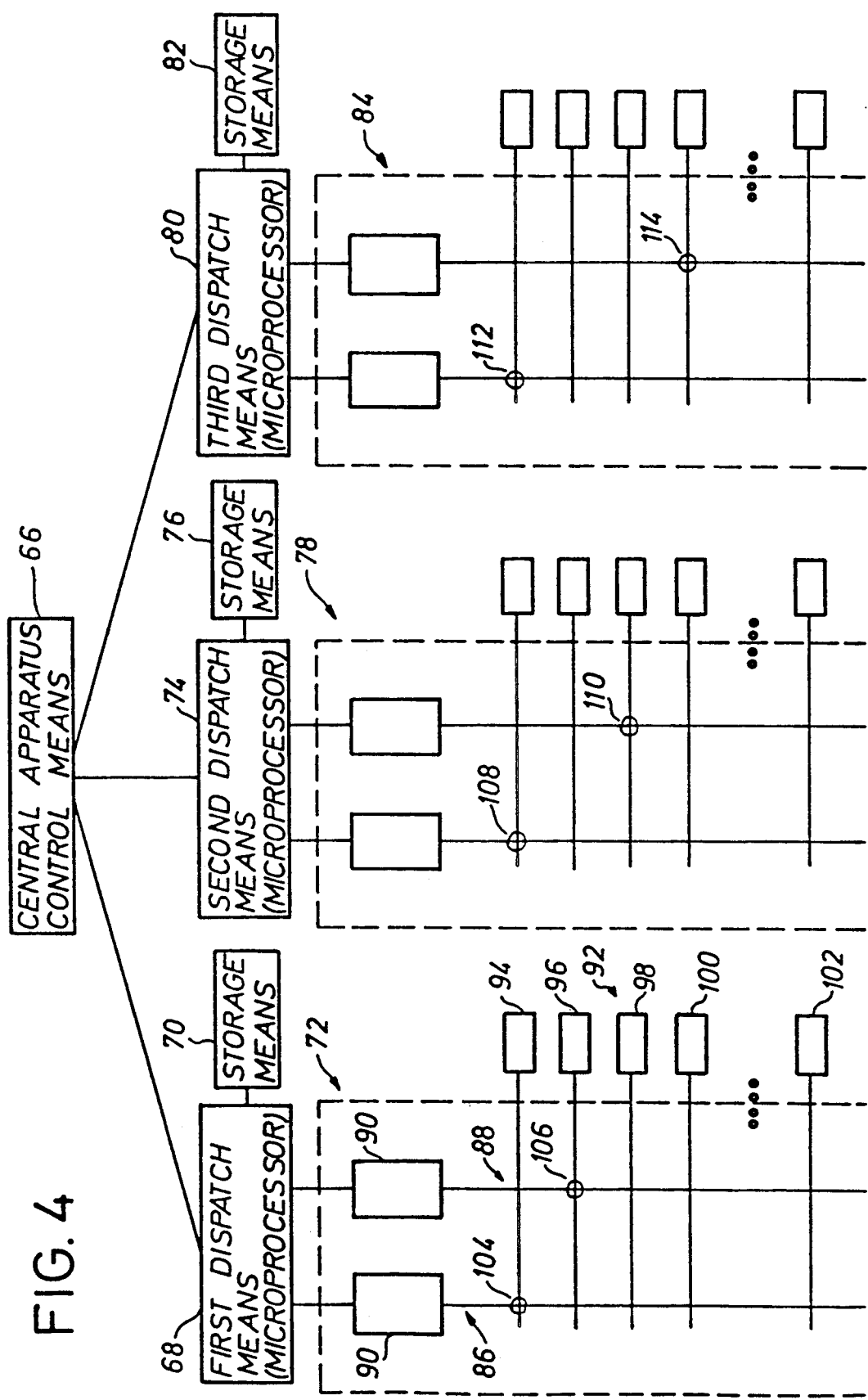
FIG. 4 is a block diagram of a titrating system including a plurality of the simultaneous dosing systems of FIG. 2.

The block diagram illustrated in FIG. 4 shows an example of a system for selecting the sequential performance of a large number of titrations. The system illustrated comprises the three units of the kind illustrated in FIG. 2. Associated with a central apparatus control means 66 is a first dispatcher 68 with associated storage unit 70 for the management and monitoring of a control-train pair 72, a second dispatcher 74 with associated storage unit 76 for the management and monitoring of a control-train pair 78, and a third dispatcher 80 with associated storage unit 82 for the management and monitoring of a control-train pair 84. The control-train pair 72 comprises a first control train 86 and a second control train 88 corresponding to control trains 44 and 46 in FIG. 2. Accordingly, the first control train 86 has a pulse length modulator 90 and a power output stage 92 with electromechanical drives 94, 96, 98, 100 and 102.

The second control train 78 is built up in a similar manner and includes a pulse length modulator 90, which, in turn, is associated with the power output stage 92.

The control-train pair 78 and 84 in terms of their configuration correspond with that of the control-train pair 72. In this figure therefore the corresponding reference symbols for the individual elements of these control trains have been omitted for the sake of clarity.

Various matchup possibilities are indicated by circuit connections 104, 106, 108, 110, 112, and 114. Each control-train pair 72,, 78, and 84 is designed for the alternating supply of the drives 94, 96, 98, 100, and 102. Because of the free selectability of the association, a user now has the possibility of simultaneously performing a large number of titrations. By combining several such control-train pairs, for example, three, as illustrated in the figure, one can increase the number of possibilities many times over.

All of the above described types of generally titrating systems presume that the pulses for the DC-motor are current pulses with a constant amplitude. Because the DC-Motor has a well-known current consumption which is a linear function of the voltage and of the angular velocity, it is also possible to use a power supply without current regulation. In this case the voltage will be kept generally constant and the power regulation is done as well by the regulation of the length of the DC voltage pulse. This solution is preferably chosen when the environmental conditions which influence the power requirements of the dosing means via the changing friction are rather favorable. All of the described combinations of dosing means, control-trains and power supplies operate in a manner analogous to those with DC current pulses.

The apparatus control unit described above is used particularly advantageously in a titration apparatus as described and disclosed in the companion Duks patent application S/N 07/500,410 filed Mar. 28, 1990.

While in accordance with the Patent Statutes the preferred forms and embodiments have been illustrated and described, it will be apparent that various modifications might be made without deviating from the inventive concepts set forth above.

What is claimed is:

1. Titrating apparatus including at least two electromechanical drive means (8) for driving at least two titrating agent dosing devices (6), respectively, comprising:
   (a) at least two titrating agent dosing means each driven by an electromechanical drive means (52-60) having a DC motor (A1-An);
   (b) means including an alternating power supply (N) and pulse length modulating means (48, 48') for supplying said DC motors with DC current pulses) A1', A2') of constant amplitude, thereby to effect the simultaneous dosing of at least two titrating agents, the lengths of the DC current pulses supplied to said DC motors, respectively, being less than 50% of the period duration (T) of the alternating power supply; and
   (c) means (30, 34) for modifying the lengths of said DC current pulses as a function of the frictional characteristics of said electromechanical drive means, respectively.

2. Apparatus as defined in claim 1, and further including a plurality of pairs of control trains (74, 78, 84) for selectively operating a relatively large number of pairs of said electromechanical drive means (94-102), respectively, each of said pairs of control trains including pairs of said pulses length modulating means (90) for supplying DC current pulses to selected pairs of said electromechanical drive means, respectively; and central control means (66) for selectively operating said control train pairs, respectively.

3. Titrating apparatus including at least two electromechanical drive means (8) for driving at least two titrating agent dosing devices (6), respectively, comprising:
   (a) at least two titrating agent dosing means each driven by an electromechanical drive means (52-60) having a DC motor (A1-An);
   (b) means including an alternating power supply (N) and pulse length modulating means (48, 48') for supplying said DC motors with DC current pulses (A1', A2') of constant amplitude, thereby to effect the simultaneous dosing of at least two titrating agents; and
   (c) means (30,34) for modifying the lengths of said DC current pulses as a function of the frictional characteristics of the associated electromechanical drive means, respectively;
   (d) said DC current pulses being supplied to said electromechanical drive means in such a manner that each electromechanical drive means, in succession, receives a DC current pulses having a length per period duration (T) of said alternating power supply (N) corresponding with the quotient of said period duration (T) divided by the number of electrochemical drive means.

4. Titrating apparatus including at least two electromechanical drive means (8) for driving at least two titrating agent dosing means (6), respectively, comprising:
   (a) at least two titrating agent dosing means each driven by an electromechanical drive means (52-60) having a DC motor (A1-An);
   (b) means including an alternating power supply (N) and pulse length modulating means (48, 48') for supplying said DC motors with DC voltage pulses of constant amplitude, thereby to effect the simultaneous dosing of at least two titrating agents, the lengths of the DC voltage pulses supplied to said DC motors, respectively, being less than 50% of the period duration (T) of the alternating power supply (N); and
   (c) means (30, 34) for modifying the lengths of said DC voltage pulses as a function of the frictional characteristics of said electromechanical drive means, respectively.

5. Apparatus as defined in claim 4, and further including a plurality of pairs of control trains (74, 78, 84) for selectively operating a relatively large number of pairs of said electromechanical drive means (94-102), respectively, each of said control trains including pairs of said pulse length modulating means (90) for supplying DC voltage pulses to selected pairs of said electromechanical drive means respectively; and central control means (66) for selectively operating said control train pairs, respectively.

6. Titrating apparatus including at least two electrochemical drive means (8) for driving at least two titrating agent dosing devices (6), respectively, comprising:
   (a) at least two titrating agent dosing means each driven by an electromechanical drive means (52-60) having a DC motor (A1-An);
   (b) means including an alternating power supply (N) and pulse length modulating means (48,48') for supplying said DC motors with DC voltage pulses (A1', A2') of constant amplitude, thereby to effect the simultaneous dosing of at least two titrating agents; and
   (c) means (30,34) for modifying the lengths of said DC voltage pulses as a function of the frictional characteristics of the associated electromechanical drive means, respectively;
   (d) said DC voltage pulses being supplied to said electromechanical drive means in such a manner that each drive means, in succession, receives a DC voltage pulse having a length, per period duration (T) of said alternating power supply, corresponding with the quotient of said period duration (T) divided by the number of electromechanical drive means.

* * * * *